United States Patent [19]

Holyoke, Jr.

[11] 4,302,451
[45] Nov. 24, 1981

[54] PESTICIDAL PHOSPHORUS SULFENAMIDES

[75] Inventor: Caleb W. Holyoke, Jr., Newark, Del.

[73] Assignee: E. I. Du Pont de Nemours and Company, Wilmington, Del.

[21] Appl. No.: 146,416

[22] Filed: May 5, 1980

[51] Int. Cl.$^3$ .................. C07F 9/24; A01N 57/30; A01N 57/32; C07D 207/10
[52] U.S. Cl. ............... 424/211; 260/326.5 A; 260/937; 260/938; 260/940; 260/944; 544/162; 546/21; 564/15; 424/209; 424/200; 424/210; 424/217; 424/256; 424/248.5; 424/274
[58] Field of Search ............. 260/944, 940, 938, 937, 260/340.9, 326.5 A; 424/211, 209, 210, 200, 217, 256, 248.5, 274; 564/15; 546/21; 544/162

[56] References Cited

U.S. PATENT DOCUMENTS 3,933,907  1/1976  Ashton et al. .................. 260/944
4,081,536  3/1978  Nelson ........................... 424/211

FOREIGN PATENT DOCUMENTS 826376  9/1975  Belgium .
846419  3/1977  Belgium .
   156  6/1978  European Pat. Off. .
  4642  3/1979  European Pat. Off. .
1455207 11/1976  United Kingdom .

Primary Examiner—Anton H. Sutto

[57] ABSTRACT

[(N,N-diarylamino)thio]phosphoramide compounds such as N-[N-[2-chloro-5-(trifluoromethyl)phenyl]-N-[2,4-dinitro-6-(trifluoromethyl)phenyl]amino thio]-N-(1-methylethyl)phosphoramidic acid, diethyl ester, are useful as miticides, insecticides, fungicides and ovicides.

48 Claims, No Drawings

PESTICIDAL PHOSPHORUS SULFENAMIDES

BACKGROUND OF THE INVENTION

This invention relates to miticidal, insecticial, fungicidal and ovicidal diarylsulfenamides.

Belgian Pat. No. 826,376 discloses pesticidal diphenylamine derivatives of the formula:

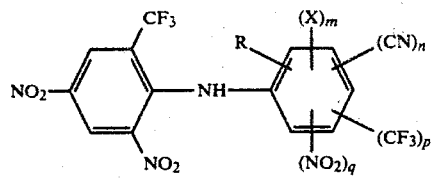

where X and R represent various substituents definitions; and British Pat. No. 1,455,207 discloses a pesticidal diphenylamine of the formula:

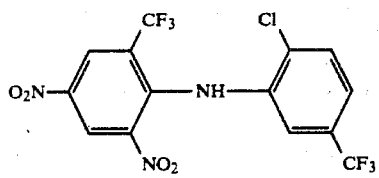

Belgian Pat. No. 846,205 discloses compounds with utility as rodenticides of the formula

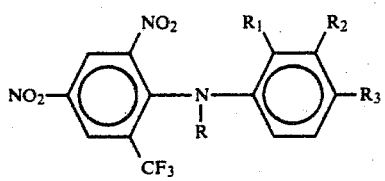

where R, $R_1$, $R_2$ and $R_3$ represent various defined substituents.

Belgian Pat. No. 846,419 discloses compounds with utility as delayed-action rodenticides.

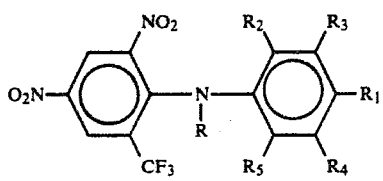

where R, $R_1$, $R_2$, $R_3$, $R_4$ and $R_5$ represent various defined substituents.

European Pat. No. 156 discloses benzotrifluoride derivatives with insecticidal, acaricidal, nematicidal, insect growth retardant, fungicidal and bactericidal activity. These compounds have the formula

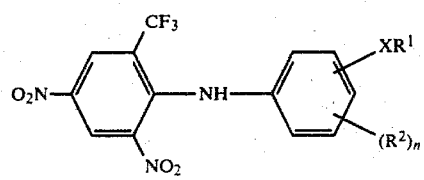

where $R^1$ and $R^2$ represent various defined substituents.

European Pat. No. 4642 discloses compounds useful as insecticides, acaricides, nematocides, fungicides and herbicides of the formula

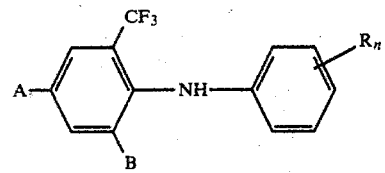

where A, B and R represent various defined substituents.

SUMMARY

According to this invention, compounds of the following formula have been discovered which are highly active miticides, insecticides, ovicides, and/or fungicides, and which cause minimal damage to desired crops.

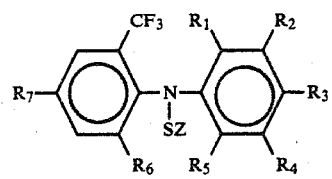

wherein $R_1$, $R_3$ and $R_4$ are independently H, F, Cl, Br, $NO_2$, $CF_3$, $OCHF_2$, $OCF_3$, $OCF_2CF_2H$ or $S(O)_kR_9$; or $R_3$ and $R_4$ may be taken together to form $-OCF_2O-$ or $-OCF_2OCF_2-$;

$R_2$ is H, F, Cl, Br, $NO_2$, $CF_3$ or $S(O)_kR_9$;

$R_5$ is H, Cl, F, Br or $NO_2$;

$R_6$ is H, $NO_2$ or $CF_3$;

$R_7$ is $NO_2$ or $CF_3$;

k is 0, 1 or 2;

$R_9$ is $C_1-C_2$ alkyl optionally substituted with 2–4 Cl and/or F;

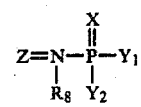

where $R_8$ is $C_1-C_8$ alkyl optionally substituted with F, Br, Cl or I, CN, $OCH_3$, $OCH_2CH_3$; phenyl or benzyl, each can be optionally substituted with Cl, F, Br, I, $CH_3$, $OCH_3$, $NO_2$ or $CF_3$,

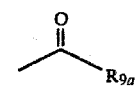

where $R_{9a}$ is $C_1-C_4$ alkyl or phenyl optionally substituted with F, Cl, Br, I, $NO_2$, $CH_3$, $OCH_3$ or $CF_3$;

X is O or S;

$Y_1$ or $Y_2$ are independently: $C_1-C_4$ alkyl optionally substituted with one or more F, Cl, Br or I, $OCH_3$, $OCH_2CH_3$, CN, $CH_3S$, $CH_3CH_2S$; $C_2-C_4$ alkenyl optionally substituted with one or more F, Cl, carboxy or carboalkoxy; benzyl which can be optionally substituted with F, Cl, Br, I, $NO_2$, $CH_3$, $OCH_3$ or $CF_3$;

$C_1$–$C_4$ alkoxy optionally substituted with one to three atoms of F, Cl, Br, $CH_3O$, $CH_3CH_2O$ or combinations thereof; $C_1$–$C_4$ thioalkyl optionally substituted with one to three of the groups F, Cl, Br, I carboxy or carboalkoxy, or combinations thereof; phenyl, phenoxy or thiophenoxy each optionally substituted with one to three of the groups F, Cl, Br, I, $NO_2$, $CH_3$, $CF_3$ or combinations thereof; or $NR_{10}R_{11}$ where $R_{10}$ is $C_1$–$C_4$ alkyl or $OCH_3$;
$R_{11}$ is $C_1$–$C_4$ alkyl and
$R_{10}$ and $R_{11}$ can be taken together to form

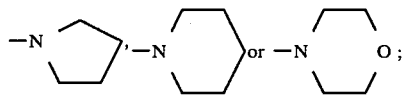

$Y_1$ and $Y_2$ can be taken together to form

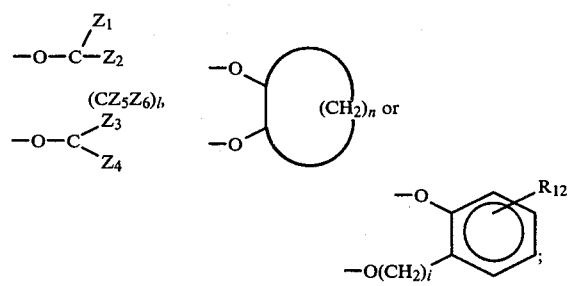

and $R_{12}$ is H, $C_1$–$C_4$ Alkyl, $C_1$–$C_4$ Alkoxy or Halogen where $Z_1$, $Z_2$, $Z_3$, $Z_4$, $Z_5$ or $Z_6$ are independently H, $CH_3$ or $CH_3CH_2$;
n is 3 or 4;
l is 0 or 1;
provided that
(1) at least two of $R_1$, $R_2$, $R_3$, $R_4$ and $R_5$ are hydrogen;
(2) no more than two of the substituents $R_1$, $R_2$, $R_3$ and $R_4$ are simultaneously $NO_2$ or $CF_3$;
(3) when two $NO_2$ or two $S(O)_kR_9$ groups are present, they are not ortho to one another;
(4) $R_6$ and $R_7$ are not simultaneously $CF_3$; and
(5) further provided that when $R_6$ is $NO_2$, then
 (a) $R_1$ is H, F or Cl when $R_3$ is other than H, F or Cl;
 (b) when $R_1 = R_3 = R_5$, then $R_1$, $R_3$ and $R_5$ are either H or F; and
 (c) $R_5$ is either H or F.
(6) only one of $Y_1$ and $Y_2$ is $NR_{10}R_{11}$.

Preferred Compounds

Preferred for reasons of lower cost, lower phytotoxicity and/or greater miticidal, insecticidal, ovicial and/or fungicidal activity are those compounds of Formula I where independently:

$R_1$ is F, Cl, Br, $CF_3$, $OCHF_2$, $OCF_3$, $OCF_2CF_2H$ or $S(O)_kCF_3$;
$R_2$ is H, F, Cl or Br;
$R_3$ is H, F, Cl, Br or $S(O)_kCF_3$;
$R_4$ is F, Cl, Br, $CF_3$, $OCHF_2$, $OCF_3$, $OCF_2CF_2H$ or $S(O)_kCF_3$; and
$R_6$ is $NO_2$.

More preferred for the same reasons are compounds of Formula I where independently:

$R_1$ and $R_4$ are independently Cl, $CF_3$, $OCF_3$, $OCF_2CF_2H$ or $S(O)_kCF_3$;
$R_3$ is H or $S(O)_kCF_3$;
$R_2$ and $R_5$ are H;
$R_6$ and $R_7$ are $NO_2$ Still More Preferred for the above reasons and in increasing order of preference are those compounds at the More Preferred in which
(1) $Y_1$ equals $Y_2$
(2) Compounds of Preference (1) in which $Y_1$ is $CH_3O$, $CH_3CH_2O$, $CH_3$, S, $CH_3CH_2S$,

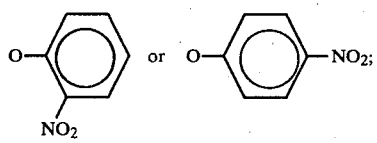

(3) Compounds of Preference (2) in which $R_8$ is $C_1$–$C_4$ alkyl;
(4) Compounds of Preference (3) in which X is O.

Specifically Preferred for reasons of excellent miticidal, fungicidal, insecticidal, and/or ovicidal activity and/or lowest cost and/or greatest ease of synthesis and/or lowest phytoxicity is: 5N-[N-[2-Chloro-5-(trifluoromethyl)phenyl]-N-[2,4-dinitro-6-(trifluoromethyl)phenyl]aminothio]-N-(1-methylethyl)phosphoramidic acid, diethyl ester.

Synthesis

The compounds of this invention can be prepared by reacting a diphenylamine of Formula II with sulfenyl chlorides, ClSZ, in the presence of an acid acceptor and an inert solvent as outlined in the following equation:

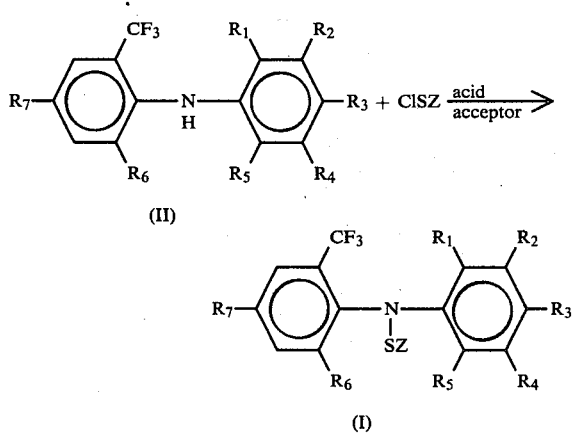

in which $R_1$, $R_2$, $R_3$, $R_4$, $R_5$, $R_6$, $R_7$, and Z are as previously defined. Organic bases such as N,N-dimethylaniline, triethylamine, trimethylamine, or pyridine or inorganic bases such as sodium or potassium hydroxide sodium or potassium carbonate, or sodium hydride may be used as the acid acceptor. Aprotic solvents such as diethyl ether, tetrahydrofuran (THF), dioxane, methylene chloride, chloroform, or toluene are exemplary of suitable solvents for the reaction. The reaction temperature can be within the range of approximately −40° C. to 80° C., preferably approximately −20° C. to 30° C. Pressure is not critical; for convenience, ambient pressure is preferred.

The diphenylamines of Formula II used in the reactions described above can be prepared using procedures taught in Belgian Pat. No. 826,376, West German Offenlegungsschrift No. 2,823,168, European Patent Application No. 156, and European Patent Application No. 4,642, the disclosures of which are herein incorporated by reference.

The sulfenyl chlorides, ClSZ, used in the preparation of the compounds of Formula I may be prepared by any of several methods well known in the art; such methods have been reviewed in *Synthesis*, 11, 561–580 (1970) or in Belgian Pat. Nos. 873,911 and 860,894.

The following examples further illustrate the preparation of compounds of Formula I. In the examples, all parts are by weight and temperatures are in degrees Centigrade unless otherwise indicated.

Preparation of the Sulfenyl Chloride

N-isopropyl phosphoramidic acid diethylester (1.95 g) and sulfur dichloride (1.03 g) were dissolved in 25 ml methylene chloride. A solution of 0.95 g of pyridine in 5 ml methylene chloride was added dropwise. The reaction mixture was stirred overnight, cooled, filtered, and solvent was removed from the filtrate in vacuum, leaving an orange-yellow solid. The solid was dissolved in toluene (20 ml) and filtered to give a toluene solution of the sulfenyl chloride.

Sulfenylation of the Diphenylamine

A 0.58 g quantity of NaH (50% dispersion in mineral oil) was rinsed with hexane and stirred in tetrahydrofuran (THF) under nitrogen. To this slurry was added 4.3 g of N-[2-chloro-5-(trifluoromethyl)phenyl]-2,4-dinitro-6-(trifluoromethyl)benzenamine in portions. The reaction mixture was stirred for 30 minutes and then cooled to $-20°$ C.

The toluene solution of the sulfenyl chloride was added to the THF solution of the diphenylamine sodium salt. The reaction mixture was stirred cold for 1 hour, cooling was removed and the reaction was stirred an additional hour. The reaction mixture was filtered through celite and solvent was removed in vacuum leaving a brown oil. Chromatography on silica gel yielded the desired product as a yellow oil which solidified on trituration with hexanes (m 109°–122° C.).

TABLE I $$R_7-\text{(ring with } CF_3, R_6\text{)}-N(SZ)-\text{(ring with } R_1, R_2, R_3, R_4, R_5\text{)} \quad Z = N-\overset{X}{\underset{R^8}{P}}\!\!\!<\!\!\begin{array}{l}Y_1\\Y_2\end{array}$$

| $R_1$ | $R_2$ | $R_3$ | $R_4$ | $R_5$ | $R_6$ |
|---|---|---|---|---|---|
| Cl | H | H | $CF_3$ | H | H |
| Cl | H | H | $CF_3$ | H | $NO_2$ |
| Cl | H | —$OCF_2O$— | | H | $NO_2$ |
| Cl | H | H | $CF_3$ | H | $CF_3$ |
| Cl | H | —$OCF_2OCF_2$— | | | $NO_2$ |
| Cl | H | H | $CF_3O$ | H | $NO_2$ |
| Cl | H | H | $HCF_2CF_2O$ | H | $NO_2$ |
| Cl | H | H | $CH_3S$ | H | $NO_2$ |
| Cl | H | H | $CHCl_2CCl_2S$ | H | $NO_2$ |
| Cl | H | H | $CF_3SO_2$ | H | $NO_2$ |
| Cl | H | H | $C_2H_5S$ | H | $NO_2$ |
| $CF_3O$ | H | H | Cl | H | $NO_2$ |
| $HCF_2CF_2O$ | H | H | Cl | H | $NO_2$ |
| $CHCl_2CCl_2S$ | H | H | Cl | H | NO |
| $CF_3S$ | H | H | H | H | $NO_2$ |
| $CH_3SO_2$ | H | H | H | H | $NO_2$ |
| $CF_3$ | H | H | H | H | $NO_2$ |
| H | H | $CF_3S$ | H | H | $NO_2$ |
| Cl | H | H | $CHF_2O$ | H | $NO_2$ |
| H | H | $HCF_2CF_2O$ | H | H | $NO_2$ |
| H | H | $CH_3S$ | H | H | $NO_2$ |
| H | H | $C_2H_5SO_2$ | H | H | $NO_2$ |
| H | $CF_3$ | Cl | H | H | $NO_2$ |
| Cl | H | Cl | H | H | $NO_2$ |
| H | Br | H | H | Br | $CH_3$ |
| F | H | F | H | F | $NO_2$ |
| H | H | Cl | H | $NO_2$ | $CH_3$ |
| Cl | H | H | $NO_2$ | H | $NO_2$ |
| H | $NO_2$ | H | H | Cl | $CH_3$ |
| H | Cl | Cl | H | H | $NO_2$ |
| H | F | H | H | F | $NO_2$ |
| H | $CHF_2CF_2S$ | H | H | H | $NO_2$ |
| H | $CHF_2CF_2SO_2$ | H | H | H | $NO_2$ |
| H | $CH_3S$ | H | H | H | $NO_2$ |
| Cl | H | $CF_3O$ | H | H | $NO_2$ |
| Br | H | Br | H | H | H |
| Cl | H | $NO_2$ | H | H | $NO_2$ |
| $NO_2$ | H | Cl | H | H | $NO_2$ |
| H | H | H | F | H | $NO_2$ |
| H | H | H | Br | H | $NO_2$ |
| Cl | H | H | Cl | H | $NO_2$ |
| Cl | H | H | $CF_3$ | H | $NO_2$ |
| Cl | H | H | $CF_3$ | H | $NO_2$ |
| Cl | H | H | $CF_3$ | H | $NO_2$ |

TABLE I-continued

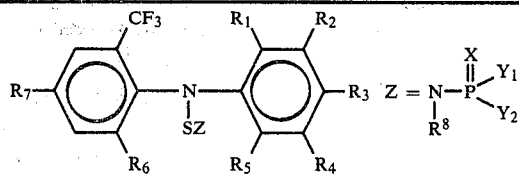

| R7 | R1 | R2 | R3 | R5 | R4 |
|---|---|---|---|---|---|
| Cl | H | H | $CF_3$ | H | $NO_2$ |
| Cl | H | H | $CF_3$ | H | $NO_2$ |
| Cl | H | H | $CF_3$ | H | $NO_2$ |
| Cl | H | H | $CF_3$ | H | $NO_2$ |
| Cl | H | H | $CF_3$ | H | $NO_2$ |
| Cl | H | H | $CF_3$ | H | $NO_2$ |
| Cl | H | H | $CF_3$ | H | $NO_2$ |
| Cl | H | H | $CF_3$ | H | $NO_2$ |
| Cl | H | H | $CF_3$ | H | $NO_2$ |
| Cl | H | H | $CF_3$ | H | $NO_2$ |
| Cl | H | H | $CF_3$ | H | $NO_2$ |
| Cl | H | H | $CF_3$ | H | $NO_2$ |
| Cl | H | H | $CF_3$ | H | $NO_2$ |
| Cl | H | H | $CF_3$ | H | $NO_2$ |
| Cl | H | H | $CF_3$ | H | $NO_2$ |
| Cl | H | H | $CF_3$ | H | $NO_2$ |
| Cl | H | H | $CF_3$ | H | $NO_2$ |
| Cl | H | H | $CF_3$ | H | $NO_2$ |

| $R_7$ | X | $R_8$ | $Y_1$ | $Y_2$ | m.p. (°C.) |
|---|---|---|---|---|---|
| $NO_2$ | O | isopropyl | $OC_2H_5$ | $OC_2H_5$ | |
| $CF_3$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | |
| $NO_2$ | O | isopropyl | $OC_2H_5$ | $OC_2H_5$ | 109–122° |
| $NO_2$ | O | $CH_3$ | phenyl | —O—⟨C$_6$H$_4$⟩—$NO_2$ | |
| $NO_2$ | S | $+CH_2)_7CH_3$ | $OCH_3$ | —S—CH(—$CO_2C_2H_5$)—$CH_2CO_2C_2H_5$ | |
| $NO_2$ | O | $\overset{O}{\underset{\|}{COCH_3}}$ | $OCH=CCl_2$ | $N(CH_3)_2$ | |
| $NO_2$ | O | 3,5-dichlorophenyl | $N(CH_3)(OCH_3)$ | —$OCH_2CH_2OC_2H_5$ | |

TABLE I-continued $$R_7 \text{-Ar}(CF_3)(R_6)\text{-N(SZ)-Ar}(R_1)(R_2)(R_3)(R_4)(R_5) \quad Z = \overset{X}{\underset{R_8}{N-P}} \begin{array}{c} Y_1 \\ Y_2 \end{array}$$

| | | | | |
|---|---|---|---|---|
| NO$_2$ | O | 4-methoxybenzyl | SCH$_3$ | —O(CH$_2$)$_3$CH$_3$ |
| NO$_2$ | O | CH$_2$CH$_2$CN | —S—C$_6$H$_4$—CF$_3$ | —(CH$_2$)$_3$CH$_3$ |
| NO$_2$ | O | C(=O)CH$_3$ | OCH$_3$ | SCH$_3$ |
| NO$_2$ | O | C(=O)C$_6$H$_4$—Br | —OCH$_2$CH$_2$SCH$_3$ | —OCH$_2$CH$_2$SCH$_3$ |
| NO$_2$ | O | t-butyl | piperidinol | —C$_6$H$_4$—CH$_3$ |
| NO$_2$ | O | C(=O)(CH$_2$)$_3$CH$_3$ | morpholinol | —O—C$_6$H$_4$—F |
| NO$_2$ | O | CH(CH$_3$)(CH$_2$CH$_3$) | O—C$_6$H$_3$Cl$_2$ | pyrrolidinol |
| NO$_2$ | S | —(CH$_2$)$_7$CH$_3$ | —CH$_3$ | SCH$_2$CH$_2$SCH$_2$CH$_2$ |
| NO$_2$ | O | C(CH$_3$)$_2$CH$_2$C(CH$_3$)$_3$ | | —OCH$_2$CH$_2$CH$_2$O— |
| NO$_2$ | O | isopropyl | | —O—CH—CH—O—, CH$_2$   CH$_2$, CH$_2$—CH$_2$ |
| NO$_2$ | O | butyl | | —O, CH$_2$—O— (benzene ring) |
| NO$_2$ | O | isopropyl | | —O, O— (benzene ring) |
| NO$_2$ | O | CH$_2$C$_6$H$_5$ | OC(CH$_3$)=CHC(=O)OCH$_3$ | OCH$_3$ |
| NO$_2$ | O | isopropyl | OCHBrCBrCl$_2$ | OCH$_3$ |
| NO$_2$ | S | isopropyl | OCH$_2$CH$_2$SC$_2$H$_5$ | OCH$_3$ |
| NO$_2$ | S | t-butyl | SCH(CO$_2$C$_2$H$_5$)CH$_2$CO$_2$H | OCH$_3$ |
| NO$_2$ | S | isopropyl | OCH(CH$_3$)CH$_2$SCH(CH$_3$)CN | OCH$_3$ |

Formulation

Useful formulations of the compounds of Formula (I) can be prepared in conventional ways. They include dusts, solutions, suspensions, emulsions, wettable powders, emulsifiable concentrates and the like. Many of these may be applied directly to the plant. Sprayable formulations can be extended in suitable media and used at spray volumes of from a few pints to several hundred gallons per acre. High-strength compositions are primarily used as intermediates for further formulation. The formulations, broadly, contain about 1% to 99% by weight of active ingredient(s) and at least one of (a) about 0.1% to 20% surfactant(s) and (b) about 1% to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High-Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Co., Ridgewood, New Jersey, as well as Sisely and Wood, "Encyclopedia of Surface Active Agents", Chemical Publ. Co., Inc., New York, 1964, list surfactants and recommended uses. All formulatiosn can contain minor amounts of additives to reduce foam, caking, corrosion, microbiological growth, promote sticking, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084).

For further information regarding the art of formulation, see for example:

J. B. Buchanan, U.S. Pat. No. 3,576,834, Apr. 27, 1971, Col, 5, Line 36 through Col. 7, Line 70 and Ex. 1–4, 17, 106, 123–140;

R. R. Shaffer, U.S. Pat. No. 3,560,616 Feb. 2, 1971, Col. 3, Line 48 through Col. 7, Line 26 and Examples 3–9, 11–18;

E. Somers, "Formulation", Chapter 6 in Torgeson, "Fungicides", Vol, I, Academic Press, New York, 1967.

EXAMPLE A

| | |
|---|---|
| N-[N-[2-chloro-5-(trifluoromethyl)phenyl]-N-[2,4-dinitro-6-(trifluoromethyl)phenyl]aminothio]-N-(1-methylethyl)phosphoramidic acid, diethyl ester | 41% |
| Dioctyl sodium sulfosuccinate | 1.5% |
| Sodium ligninsulfonate | 3% |
| Low-viscosity methyl cellulose | 1.5% |
| Kaolinite | 54% |

The ingredients are thoroughly blended, passed through to produce an average particle size under 15 microns, reblended, and sifted through a U.S.S. No. 50 sieve (0.3 mm opening) before packaging.

All compounds of the invention may be formulated in the same manner, and dispersed in water for application.

EXAMPLE B

Wettable Powder

| | |
|---|---|
| N-[N-[2-chloro-5-(trifluoromethyl)phenyl]-N-[2,4-dinitro-6-(trifluoromethyl)phenyl]aminothio]-N-(1-methylethyl)phosphoramidic acid, diethyl ester | 30% |
| Sodium alkylnaphthalenesulfonate | 2% |
| Sodium ligninsulfonate | 2% |
| Synthetic amorphous silica | 3% |
| Kaolinite | 63% |

The ingredients are combined in an efficient blender, passed through a hammer mill to produce particles below 40 microns, and then reblended. The product is sifted through a U.S.S. No. 50 sieve (0.3 mm openings) before packaging.

EXAMPLE C

Dust

| | |
|---|---|
| Wettable powder of Example A | 10% |
| Pyrophyllite (powder) | 90% |

The wettable powder and the pyrophyllite diluent are thoroughly blended and then packaged. The product is suitable for use as a dust.

EXAMMPLE D

Aqueous Suspension

| | |
|---|---|
| N-[N-[2-chloro-5-(trifluoromethyl)phenyl]-N-(2,4-dinitro-6-(trifluoromethyl)phenyl]aminothio]-N-(1-methylethyl)phosphoramidic acid, diethyl ester | 25% |
| Hydrated attapulgite | 3% |
| Crude calcium ligninsulfonate | 10% |
| Sodium dihydrogen phosphate | 0.5% |
| Water | 61.5% |

The ingredients are ground together in a sand mill until the solid particles have been reduced to diameters under 10 microns. The product may be diluted with water for spray application.

EXAMPLE E

Solution

| | |
|---|---|
| N-[N-[2-chloro-5-(trifluoromethyl)phenyl]-N-[2,4-dinitro-6-(trifluoromethyl)phenyl]aminothio]-N-(1-methylethyl)phosphoramidic acid, diethyl ester; | 30% |
| Dimethylformamide | 70% |

The ingredients are combined and stirred to produce a solution, which can be used for low volume applications.

EXAMPLE F

Granule

| | |
|---|---|
| Wettable powder of Example A | 15% |
| Gypsum | 69% |
| Potassium sulfate | 16% |

The ingredients are blended in a rotating mixer and water sprayed on to accomplish granulation. When most of the material has reached the desired range of 1.0 to 0.42 mm (U.S.S. No. 18 to 40 sieves), the granules are removed, dried and screened. Oversize material is crushed to produce additional material in the desired range. These granules contain 6.0% active ingredient.

Utility

The compounds of this invention may be used in several ways. First, they are active as miticides and mite ovicides and may be used to protect plants from damage caused by these pests. More specifically, fruits, field crops, vegetables and ornamentals can be protected.

When mite eggs or mites come into contact with the compounds of this invention, either in the form of direct spray or in the case of motile forms by walking over treated surfaces, they are killed if they have been exposed to a sufficiently high dosage. While most plants are able to tolerate the presence of very small numbers of mites without adverse effect, the reproductive capacity of these pests is enormous. Generally, mite populations rapidly build up, easily out-stripping parasite and predator capabilities for control. Growers noting rapid mite build-up must take immediate action to prevent damage to economically important crops.

The method of this invention, namely, contacting mites or mite eggs with an effective concentration, is a most desirable method for control of these pests. This may be accomplished by applying an effective amount of a compound of this invention to the locus of infestation, to the area to be protected or to the pests themselves.

The quantity of compound needed for miticidal activity will vary depending on the specific situation; generally, a very small quantity is required. Among the variables that must be considered in deciding on the quantity of chemical to be used are the specific compound itself, the specific mite to be controlled, weather conditions, the type of crop, the stage of development of the crop, the volume of spray applied, population pressure, and the interval between applications. For plant protection, solutions or suspensions contain as little as 2.5 ppm of active ingredient in a spray solution may prove effective in a given set of circumstances. For field usage, however, in high-volume applications, aqueous spray preparations containing 5-2500 ppm of active ingredient are generally useful. Preferred are suspensions containing 20-500 ppm, and most preferred are those containing 80-320 ppm. On an area basis, in general, 0.03 to 5.5 kilograms of active ingredient per hectare are acceptble, preferably 0.03 to 3 kilograms, and most preferably, 0.06 to 2 kg. When applied in an orchard, spraying is continued until run-off is observed.

The compounds are especially suited for the protection of living plants such as fruit-bearing trees, nut-bearing trees, ornamental trees, forest trees, vegetable crops, horticultural crops (including ornamentals, small fruits and berries) and grain and seed crops. Apple trees, peach trees, cotton, citrus trees, bean and peanuts are particularly susceptible to mite damage and can be protected by application of the compounds of this invention. To assure control throughout the growing season (e.g., June through August in the Northern Hemisphere) multiple applications at desired intervals can be utilized.

Many species of mites are controlled by the compounds of this invention. The following is a list of representative susceptible mites along with the types of damage that they can cause: *Panonychus ulmi* (European red mite) and *Tetranychus urticae* (two-spotted mite) which are commonly called "orchard mites", and which attack a great many deciduous trees, such as apple, pear, cherry, plum and peach trees; *Tetranychus atlanticus* (Atlantic or strawberry mite), *T. cinnabarinus* (carmine spider mite) and *T. pacificus* (Pacific mite); which attack cotton and numerous other crop plants; *Paratetranychus citri* (citrus red mite) and others which attack citrus; *Phyllocoptruta oleivora* which causes citrus rust; *Byrobia praetiosa* (clover mite) which attacks clover, alfalfa and other crops; and *Aceria Neocynodomis* which attacks grasses and other plants.

The compounds of this invention are useful for the control of insects throughout their various developmental stages. The insects or insect eggs are controlled by applying the material in a convenient formulation to the locus of infestation, to the area to be protected, or to the pests themselves. For the control of insects in agricultural crops, the compound is generally applied to the foliage or other plant parts which are to be protected. Effective amounts to be applied depend on the species to be controlled, its life stage, its size and location and other variables. In general, 0.1 to 10 kg/ha may be required for insect control in agriculture with rates of 0.25 to 4 kg/ha usually being sufficient. Preferable rates in large scale operations are in the range of 0.3 to 2 kg/ha.

The insect species that may be controlled during their various developmental stages by the insecticidal action of the compounds of this invention include, but are not limited to, *Spodoptera exigua* (beet armyworm), *Spodoptera eridania* (southern armyworm), *Spodoptera frugiperda* (fall armyworm), *Heliothis zea* (bollworm), *Heliothis virescens* (tobacco budworm), and *Trichoplusia ni* (cabbage looper).

These compounds are especially useful for controlling adult mosquitos, mosquito larvae, and ticks including, but not limited to, *Rhipicephalus sanguineus* (brown dog tick) and *Dermacentor variabiles* (American dog tick).

Motile stages of insects that may be controlled include, but are not limited to,

*Aphis fabae* (bean aphid), *Myzus persicae* (green peach aphid), *Melanopus femurrubrum* (redlegged grasshopper), and *Musca domestica* (house fly).

EXAMPLE 2

Test units consisted of plant pots containing two red kidney bean plants in the two-leaf stage per pot. The plants were infested with two spotted mites and sprayed to run-off with dispersions of N-[N-[2-Chloro-5-(trifluoromethyl)phenyl]-N-[2,4-dinitro-6-(trifluoromethyl)phenyl]aminothio]-N-(1-methylethyl)phosphoramidic acid, diethyl ester, at the indicated concentrations. Dispersions were made by dissolving weighed quantities of the active ingredients in 10 ml of acetone and then diluting to volume with water containing 1:3000 of a surfactant, DuPonol ® (a tradename of E. I. du Pont de Nemours and Co. for sodium alcohol sulfate). Mortality was evaluated two days after spraying.

| Compound | % Spray Concentration | % Mortality (2 days) |
|---|---|---|
| N-[N-[2-chloro-5-(trifluoro-methyl)phenyl]-N-[2,4-dinitro-6-(trifluoromethyl)phenyl] aminothio]-N-(1-methylethyl) phosphoramidic acid, diethyl ester | 0.0010 | 100 |

EXAMPLE 3

Egg masses of the beet armyworm (*Spodoptera exigua*), laid on cellophane, each containing 50-75 eggs, were placed on petri dishes and sprayed with solutions of N-[N-[2-chloro-5-(trifluoromethyl)phenyl]aminothio]-N-(1-methylethyl)phosphoramidic acid, diethyl ester. Dispersions were made by dissolving weighed quantities of the active ingredient in acetone. Three days later, percent control (% eggs failing to hatch) was determined.

| Compound | % Spray Concentration | % Control (3 days) |
|---|---|---|
| N-[N-[2-chloro-5-(trifluoromethyl)phenyl]-N-[2,4-dinitro-6-(trifluoromethyl)phenyl]aminothio]-N-(1-methylethyl)-phosphoramidic acid, diethyl ester | 0.00250 | 100 |

EXAMPLE 4

Tobacco budworm (*Heliothis virescens*) larvae were treated topically with N-[N-[2-chloro-5-(trifluoromethyl)phenyl]-N-[2,4-dinitro-6-(trifluoromethyl)phenyl]amino thio]-N-(1-methylethyl)phosphoramidic acid, deithyl ester. One microliter of the indicated concentration was applied to the dorsoprothoracic area of each larva tested. Stock solutions were prepared by dissolving appropriately weighed quantities of active ingredient in predetermined quantities of acetone. Further diluting with acetone yielded the desired concentrations. After treatment, the larvae were returned to cups containing artificial diet (rearing substrate) and kept in a growth room at 26°±0.5° C. and 50-60% RH. Mortality readings were taken at 48 hours.

| Compound | μg/larva | % Mortality |
|---|---|---|
| N-[N-[2-chloro-5-(trifluoromethyl)phenyl]-N-[2,4-dinitro-6-(trifluoromethyl)phenyl]aminothio]-N-(1-methylethyl)phosphoramidic acid, diethyl ester | 5.0 | 100 |

EXAMPLE 5

Beet armyworm (*Spodoptera exigua*) larvae were treated topically with N-[N-[2-chloro-5-(trifluoromethyl)phenyl]-N-[2,4-dinitro-6-(trifluoromethyl)phenyl]aminothio]-N-(1-methylethyl)phosphoramidic acid, diethyl ester. One microliter of the indicated concentration was applied to the dorsoprotoracic area of each larva tested. Stock solutions were prepared by dissolving appropriately weighed quantities of active ingredient in predetermined quantities of acetone. Further diluting with acetone yielded the desired concentrations. After treatment, the larvae were returned to cups containing artificial diet (rearing substrate) and kept in a growth room at 26°±0.5° C. and 50-60% RH. Mortality readings were taken at 48 hours.

| Compound | μg/larva | % Mortality |
|---|---|---|
| N-[N-[2-chloro-5-(trifluoromethyl)phenyl]-N-[2,4-dinitro-6-(trifluoromethyl)phenyl]aminothio]-N-(1-methylethyl)phosphoramidic acid, diethyl ester | 1 | 97 |

EXAMPLE 6

Twenty-five house fly adults are secured in screened stainless steel ring cages and treated with acetone dispersions of N-[N-[2-chloro-5-(trifluoromethyl)phenyl]-N-[2,4-dinitro-6-(trifluoromethyl)phenyl]aminothio]-N-(1-methylethyl)phosphoramidic acid, diethyl ester at the indicated concentrations. The stock dispersion is prepared by dissolving appropriately weighed quantities of active ingredient in predetermined quantities of acetone. Further diluting with acetone yields the desired concentrations. After treating, the units are kept in a room maintained at 25°±2° C., 50% RH. Results are recorded at the end of 1 day.

| Compound | Conc., % | % Mortality |
|---|---|---|
| N-[N-[2-chloro-5-(trifluoromethyl)phenyl]-N-[2,4-dinitro-6-(trifluoromethyl)phenyl]aminothio]-N-(1-methylethyl)phosphoramidic acid, diethyl ester | .01 | 100 |

The compounds of this invention are also useful as plant disease control agents. They are effective for the control of a broad spectrum of plant diseases as represented by, but not limited to, soil-borne fungal pathogen *Rhizoctonia solani*, foliar pathogens, *Puccinia graminis*, *Erisyphe cichoracearum*, *Venturia inaequalis* and *Phytophthora infestans*, and the seedborne fungus *Helminthosporium oryzae*. Diseases of a wide variety of ornamental, vegetable, cereal and fruit crops are controlled by the compound of this invention.

Disease control is accomplished by applying the compounds to the portion of the plant to be protected, such as the roots, stems, foliage, fruit, seeds, tubers or bulbs, or to the media (soil or sand) in which the plants to be protected are growing. The compounds may also be applied to the seed from which the plants to be protected are to be grown.

Rates of application for the compounds will be influenced by many factors of the environment and must be determined under use conditions. Foliage can normally be protected when treated at a rate of from 1 to 500 ppm of active ingredient. Plants growing in soil treated at a concentration of from 0.1 to about 20 kg/ha can be protected from disease. Seed and seedlings can normally be protected when seed is treated at a rate of from 0.06 to about 3 grams per kilogram of seed.

EXAMPLE 7

Rice seed infected with *Helminthosporium oryzae* are treated with a comound of this invention at a rate of 1.3 g per kilogram of seed. This is accomplished by soaking infected seed for 1 minute in a suspension of the indicated compound dissolved in a solution containing 4% glycerine, 4% water, 0.02% Tween®20*, and 92% acetone. Treated seed are placed on moist blotters and enclosed in plastic bags for 18 days at which time disease ratings are made based on percent germination. As shown in the following table, the compound of this invention provided excellent disease control, as treated seed had a high percentage germination in contrast to untreated seed which did not germinate. Phytotoxicity in the form of growth reduction was observed on germinated seedlings in association with disease control.

*Tween®20 is a trademark of ICI Americas, Inc., and consists of polyoxyethylene (2) sorbitan monolaurate.

| Compound | % Control of rice Helminthosporium in a seed treatment test |
|---|---|
| N-[N-[2-Chloro-5-(trifluoromethyl)phenyl]-N-[2,4-dinitro-6-(trifluoromethyl)phenyl]aminothio]-N-(1-methylethyl)phosphoramidic acid, diethyl ester | 100 (G) |

*G = growth reduction

EXAMPLE 8

Rhizoctonia solani-infested soil was placed in a 900 cc cup. A compound of this invention was mixed at a rate of 15 kg/ha in a section 2" wide × 2" deep × 4" long to simulate an in-the-row application. Five cotton seeds were planted in the treated soil. After 8 days, the cotton plants were removed and rated for disease control. Phytotoxicity in the form of growth reduction was observed on plants in association with disease control.

| Compound | % Rhizoctonia solani control |
|---|---|
| N-[N-[2-chloro-5-(trifluoromethyl)phenyl]-N-[2,4-dinitro-6-(trifluoromethyl)phenyl]aminothio]-N-(1-methylethyl)phosphoramidic acid, diethyl ester | 100 (G) |

*G = Growth reduction

EXAMPLE 9

A compound of this invention is dissolved in acetone in an amount equal to 6% of the final volume and then suspended at a concentration of 20 ppm in purified water contining 25 ppm of the surfactant Alkanol® XC (sodium alkyl naphthalene sulfonate). This suspension is sprayed to the point of run-off on apple seedlings. The following day, the plants are inoculated with a spore suspension of the fungus *Venturia inaequalis* and incubated in a growth room for 10–12 days. Disease ratings are then made. As shown in the following table, the compound of this invention provided excellent disease control, as treated plants had no apple scab lesions in contrast to untreated plants which were covered with scab lesions. Phytotoxicity in the form of foliar burn was observed on the plants in association with disease control.

| Compounds | % Control of Apple Scab in a Preventive test |
|---|---|
| N-[N-[2-chloro-5-(trifluoromethyl)phenyl]-N-[2,4-dinitro-6-(trifluoromethyl)phenyl]aminothio]-N-(1-methylethyl)phosphoramidic acid, diethyl ester | 100 (B) |

*Burn = B

EXAMPLE 10

A compound of this invention is dissolved in acetone in an amount equal to 6% of the final volume and then suspended at a concentration of 20 ppm in purified water containing 25 ppm of the surfactant Alkanol® XC (sodium alkyl naphthalene sulfonate). This suspension is sprayed to the point of run-off on apple seedlings. The following day, ½ inch of simulated rainfall is applied to the foilage of the plants. When the foliage is dry, the plants are inoculated with a spore suspension of the fungus *Venturia inaequalis* and incubated in a growth room for 10–12 days. Disease ratings are then made. As shown in the following table, the compound of this invention provided excellent disease control, as treated plants had no apple scab lesions in contrast to untreated plants which were covered with scab lesions. Phytotoxicity in the form of foliar burn was observed on the plants in association with disease control.

| Compounds | % Control of Apple scab in a residual wash-off test |
|---|---|
| N-[N-[2-chloro-5-(trifluoromethyl)phenyl]-N-[2,4-dinitro-6-(trifluoromethyl)phenyl]aminothio]-N-(1-methylethyl)phosphoramidic acid, diethyl ester | 100 (B) |

*B = Burn

EXAMPLE 11

A compound of this invention is dissolved in acetone in an amount equal to 6% of the final volume and then suspended at a concentration of 20 ppm in purified water containing 25 ppm of the surfactant Alkanol® XC (sodium alkyl naphthalene sulfonate). This suspension is sprayed to the point of run-off on apple seedlings. When the foliage is dry, the plants are exposed to 3500 foot candles of light from a xenon arc source for a period of 16 hours. This light source approximates the spectrum of natural sunlight, and is used to assess photostability of the compound of this invention on plant foliage. The following day, the plants are inoculated with a spore suspension of the fungus *Venturia inaequalis* and incubated in a growth room for 10–12 days. Disease ratings are then made. As shown in the following table, the compound of this invention provided excellent disease control, the treated plants had no apple scab lesions in contrast to untreated plants which were covered with scab lesions. Phytotoxicity in the form of foliar furn was observed on the plants in association with disease control.

| Compound | % control of apple scab in a photostability test |
|---|---|
| N-[N-[2-chloro-5-(trifluoromethyl)phenyl]-N-[2,4-dinitro-6-(trifluoromethyl)phenyl]aminothio]-N-(1-methylethyl)phosphoramidic acid, diethyl ester | 100 (B) |

*B = burn

EXAMPLE 12

A compound of this invention are dissolved in acetone in an amount equal to 6% of the final volume and then suspended at a concentration of 20 ppm in purified water containing 25 ppm of the surfactant Alkanol® XC (sodium alkyl naphthalene sulfonate). This suspension is sprayed to the point of run-off on cucumber seedlings. The following day, the plants are inoculated with a spore suspension of the fungus *Erysiphe cichoracearum* and incubated in a growth room for 7 days.

Disease ratings are then made. As shown in the following table, the compound of this invention provided excellent disease control, as treated plants had no powdery mildew in contrast to untreated plants which were covered with powdery mildew. Phytotoxicity in the form of foliar burn or growth reduction was observed on the plants in association with disease control.

| Compound | % Control Cucumber Powdery Mildew in a Preventive Test |
|---|---|
| N-[N-[2-chloro-5-(trifluoromethyl)phenyl]-N-[2,4-dinitro-6-(trifluoromethyl)phenyl]aminothio]-N-(1-methylethyl)phosphoramidic acid, diethyl ester | 100 (B) |

*B = burn

EXAMPLE 13

A compound of this invention is dissolved in acetone in an amount equal to 6% of the final volume and then suspended at a concentration of 20 ppm in purified water containing 25 ppm of the surfactant Alkanol ® XC (sodium alkyl naphthalene sulfonate). This suspension is sprayed to the point of run-off on cucumber seedlings. The following day, ½ inch of simulated rainfall is applied to the foliage of the plants. When the foliage is dry, the plants are inoculated with a spore suspension of the fungus *Erysiphe cichoracearum* and incubated in a growth room for 7 days. Disease ratings are then made. As shown in the following table, the compound of this invention provided excellent disease control, as treated plants had little powdery mildew in contrast to untreated plants which were covered with powdery mildew. Phytotoxicity in the form of foliar burn was observed on plants in association with disease control.

| Compound | % Control Cucumber Powdery Mildew in a Residual Wash-Off Test |
|---|---|
| N-[N-[2-chloro-5-(trifluoromethyl)phenyl]-N-[2,4-dinitro-6-(trifluoromethyl)phenyl]aminothio]-N-(1-methylethyl)phosphoramidic acid, diethyl ester | 82 (B) |

*B = burn

EXAMPLE 14

A compound of this invention is dissolved in acetone in an amount equal to 6% of the final volume and then suspended at a concentration of 20 ppm in purified water containing 25 ppm of the surfactant Alkanol ® XC (sodium alkyl naphthalene sulfonate). This suspension is sprayed to the point of run-off on cucumber seedlings. When the foliage is dry, the plants are exposed to 3500 foot candles of light from a xenon arc source for a period of 16 hours. This light source approximates the spectrum of natural sunlight, and is used to assess photostability of the compound of this invention on plant foliage. The following day, the plants are inoculated with a spore suspension of the fungus *Erysiphe cichoracearum* and incubated in a growth room for 7 days. Disease ratings are then made. As shown in the following table, the compound of this invention provided excellent disease control, as treated plants had little powdery mildew in contrast to untreated plants which were covered with powdery mildew. Phytotoxicity in the form of foliar burn was observed on plants in association with disease control.

| Compound | % Control Cucumber Powdery Mildew in a Photostability Test |
|---|---|
| N-[N-[2-chloro-5-(trifluoromethyl)phenyl]-N-[2,4-dinitro-6-(trifluoromethyl)phenyl]aminothio]-N-(1-methylethyl)phosphoramidic acid, diethyl ester | 99 (B) |

*B = Burn

EXAMPLE 15

A compound of this invention is dissolved in acetone in an amount equal to 6% of the final volume and then suspended at a concentration of 20 ppm in purified water containing 25 ppm of the surfactant Alkanol ® XC (sodium alkyl naphthalene sulfonate). This suspension is sprayed to the point of run-off on wheat seedlings. The following day, the plants are inoculated with a spore suspension of *Puccinia graminis* var. tritici and incubated in a saturated humidity chamber at 20° C. for 24 hours and then in a growth room for an additional 7 days, when disease ratings were made. As shown in the following table, the compound of this invention provided excellent disease control. Treated plants had few rust pustules while the untreated plants had numerous rust pustules on each leaf.

| Compound | % Control Wheat Rust In a Preventive Test |
|---|---|
| N-[N-[2-chloro-5-(trifluoromethyl)phenyl]-N-[2,4-dinitro-6-(trifluoromethyl)phenyl]aminothio]-N-(1-methylethyl)phosphoramidic acid, diethyl ester | 97 |

EXAMPLE 16

A compound of this invention is dissolved in acetone in an amount equal to 6% of the final volume and then suspended at a concentration of 20 ppm in purified water containing 25 ppm of the surfactant Alkanol ® XC (sodium alkyl naphthalene sulfonate). This suspension is sprayed to the point of run-off on wheat seedlings. The following day, ½ inch of simulated rainfall is applied to the foliage of the plants. When the foliage is dry, the plants are innoculated with a spore suspension of *Puccinia graminis* var. tritici and incubated in a saturated humidity chamger at 20° C. for 24 hours and then in a growth room for an additional 7 days, when disease ratings were made. As shown in the following table, the compound of this invention provided excellent disease control. Treated plants had no rust pustules while the untreated plants had numerous rust pustules on each leaf.

| Compound | % Control Wheat Rust in a Residual Wash-Off Test |
|---|---|
| N-[N-[2-Chloro-5-(trifluoromethyl)phenyl]-N-[2,4-dinitro-6-(trifluoromethyl)phenyl]aminothio]-N-(1-methylethyl) | 100 |

-continued

| Compound | % Control Wheat Rust in a Residual Wash-Off Test |
|---|---|
| phosphoramidic acid, diethyl ester | |

EXAMPLE 17

A compound of this invention is dissolved in acetone in an amount equal to 6% of the final volume and then suspended at a concentration of 20 ppm in purified water containing 25 ppm of the surfactant Alkanol® XC (sodium alkyl naphthalene sulfonate). This suspension is sprayed to the point of run-off on wheat seedlings. When the foliage is dry, the plants are exposed to 3500 foot candles of light from a xenon arc source for a period of 16 hours. This light source approximates the spectrum of natural sunlight, and is used to assess photostability of the compound of this invention on plant foliage. The following day, the plants are inoculated with a spore suspension of *Puccinia graminis* var. tritici and incubated in a saturated humidity chamber at 20° C. for 24 hours and then in a growth room for an additional 7 days, when disease ratings were made. As shown in the following table, the compound of this invention provided excellent disease control. Treated plants had few rust pustules while the untreated plants had numerous rust pustules on each leaf.

| Compound | % Control Wheat Rust in a Photostability test |
|---|---|
| N-[N-[2-chloro-5-(trifluoromethyl)phenyl]-N-[2,4-dinitro-6-(trifluoromethyl)phenyl]aminothio]-N-(1-methylethyl)phosphoramidic acid, diethyl ester | 96 |

EXAMPLE 18

A compound of this invention is dissolved in acetone in an amount equal to 6% of the final volume and then suspended at a concentration of 5 ppm in purified water containing 25 ppm of the surfactant Alkanol® XC (sodium alkyl naphthalene sulfonate). This suspension is sprayed to the point of run-off on tomato seedlings. The following day, the plants are inoculated with a spore suspension of the fungus *Phytophthora infestans* and incubated in a growth room for 4 days. Disease ratings are then made. As shown in the following table, the compound of this invention provided excellent disease control, as treated plants had few late blight lesions in contrast to untreated plants which were covered with lesions. Phytotoxicity in the form of foliar burn was observed on the plants in association with disease control.

| Compound | % Control Tomato Late Blight In a Preventive Test |
|---|---|
| N[N-[2-chloro-5-(trifluoromethyl)phenyl]-N-[2,4-dinitro-6-(trifluoromethyl)phenyl]aminothio]-N-(1-methylethyl)phosphoramidic acid, diethyl ester | 90 (B) |

*B = burn

What is claimed is:

1. A compound of the formula 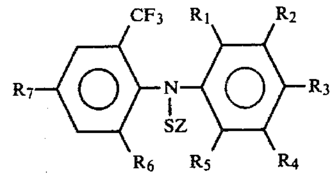 (I)

wherein $R_1$, $R_3$ and $R_4$ are independently H, F, Cl, Br, $NO_2$, $CF_3$, $OCHF_2$, $OCF_3$, $OCF_2CF_2H$ or $S(O)_kR_9$; or $R_3$ and $R_4$ may be taken together to form $-OCF_2O-$ or $-OCF_2OCF_2-$;

$R_2$ is H, F, Cl, Br, $NO_2$, $CF_3$ or $S(O)_kR_9$;

$R_5$ is H, Cl, F, Br or $NO_2$;

$R_6$ is H, $NO_2$ or $CF_3$;

$R_7$ is $NO_2$ or $CF_3$;

k is 0, 1 or 2;

$R_9$ is $C_1$–$C_2$ alkyl optionally substituted with 2-4 Cl and/or F;

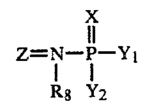

where $R_8$ is $C_1$–$C_8$ alkyl optionally substituted with F, Br, Cl or I, CN, $OCH_3$, $OCH_2CH_3$; phenyl or benzyl, each can be optionally substituted with Cl, F, Br, I, $CH_3$, $OCH_3$, $NO_2$ or $CF_3$;

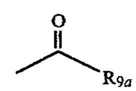

where $R_{9a}$ is $C_1$–$C_4$ alkyl or phenyl optionally substituted with F, Cl, Br, I, $NO_2$, $CH_3$, $OCH_3$ or $CF_3$;

X is O or S;

$Y_1$ or $Y_2$ are independently: $C_1$–$C_4$ alkyl optionally substituted with one or more F, Cl, Br or I, $OCH_3$, $OCH_2CH_3$, CN, $CH_3S$, $CH_3CH_2S$; $C_2$–$C_4$ alkenyl optionally substituted with one or more F, Cl, carboxy or carboalkoxy; benzyl which can be optionally substituted with F, Cl, Br, I, $NO_2$, $CH_3$, $OCH_3$ or $CF_3$; $C_1$–$C_4$ alkoxy optionally substituted with one to three atoms of F, Cl, Br, $CH_3O$, $CH_3CH_2O$ or combinations thereof;

$C_1$–$C_4$ thioalkyl optionally substituted with one to three of the groups F, Cl, Br, I, carboxy or carboalkoxy, or combinations thereof; phenyl, phenoxy or thiophenoxy each optionally substituted with one to three of the groups F, Cl, Br, I, $NO_2$, $CH_3$, $CF_3$ or combinations thereof; or $NR_{10}R_{11}$ where $R_{10}$ is $C_1$–$C_4$ alkyl or $OCH_3$;

$R_{11}$ is $C_1$–$C_4$ alkyl; and $R_{10}$ and $R_{11}$ can be taken together to form ,  or ;

$Y_1$ and $Y_2$ can be taken together to form

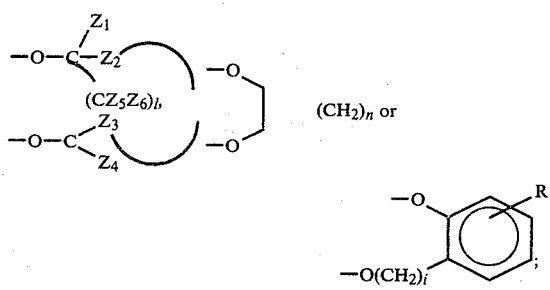 $(CH_2)_n$ or

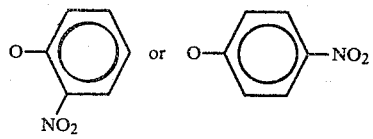

$-O(CH_2)_i$ —⟨ ⟩—$R_{12}$ ;

and $R_{12}$ is H, $C_1-C_4$ alkyl, $C_1-C_4$ Alkoxy or Halogen where $Z_1$, $Z_2$, $Z_3$, $Z_4$, $Z_5$ or $Z_6$ are independently H, $CH_3$ or $CH_3CH_2$;

n is 3 or 4;

l is 0 or 1;

provided that (1) at least two of $R_1$, $R_2$, $R_3$, $R_4$ and $R_5$ are hydrogen;

(2) no more than two of the substituents $R_1$, $R_2$, $R_3$ and $R_4$ are simultaneously $NO_2$ or $CF_3$;

(3) when two $NO_2$ or two $S(O)_k R_9$ groups are present, they are not ortho to one another;

(4) $R_6$ and $R_7$ are not simultaneously $CF_3$; and (5) further provided that when $R_6$ is $NO_2$, then
  (a) $R_1$ is H, F or Cl when $R_3$ is other than H, F or Cl;
  (b) when $R_1 = R_3 = R_5$, then $R_1$, $R_3$ and $R_5$ are either H or F; and
  (c) $R_5$ is either H or F.

(6) when $R_{10}$ is $OCH_3$, $R_{11}$ is $C_1-C_4$ alkyl;

(7) only one of $Y_1$ and $Y_2$ is $NR_{10}R_{11}$;

(8) only one of $R_{10}$ and $R_{11}$ is phenyl or substituted phenyl.

2. A compound of claim 1 wherein $R_1$ is F, Cl, Br, $CF_3$, $OCHF_2$, $OCF_3$, $OCF_2CF_2H$ or $S(O)_k CF_3$.

3. A compound of claim 1 wherein $R_2$ is H, F, Cl or Br.

4. A compound of claim 1 wherein $R_3$ is H, F, Cl, Br or $S(O)_k CF_3$.

5. A compound of claim 1 wherein $R_4$ is F, Cl, Br, $CF_3$, $OCHF_2$, $OCF_3$, $OCF_2CF_2H$ or $S(O)_k CF_3$.

6. A compound of claim 1 wherein $R_6$ is $NO_2$.

7. A compound of claim 1 wherein $R_1$ and $R_4$ are independently Cl, $CF_3$, $OCF_3$, $OCF_2CF_2H$ or $S(O)_k CF_3$.

8. A compound of claim 1 wherein $R_3$ is H or $S(O)_k CF_3$.

9. A compound of claim 1 wherein $R_2$ and $R_5$ are H.

10. A compound of claim 1 wherein $R_6$ and $R_7$ are $NO_2$.

11. A compound of claim 10 wherein
$R_1$ and $R_4$ are independently Cl, $CF_3$, $OCF_3$, $OCF_2CF_2H$ or $S(O)_k CF_3$;
$R_3$ is H or $S(O)_k CF_3$;
$R_2$ and $R_5$ are H;
$R_6$ and $R_7$ are $NO_2$.

12. A compound of claim 11 wherein $Y_1 = Y_2$.

13. A compound of claim 12 wherein $Y_1$ is $CH_3O$, $CH_3CH_2O$, $CH_3S$, $CH_3CH_2S$, 14. A compound of claim 13 wherein $R_8$ is $C_1-C_4$ alkyl.

15. A compound of claim 14 wherein X is O.

16. The compound of claim 1 which is N-[N-[2-Chloro-5-(trifluoromethyl)phenyl]-N-[2,4-dinitro-6-(trifluoromethyl)phenyl]aminothio]-N-(1-methylethyl)-phosphoramidic acid, diethyl ester.

17. A method for control of mites, insects, fungus, mite eggs or insect eggs which comprises applying to a locus to be protected a miticidally, insecticidally, fungicidally or ovicidally effective amount of a compound of claim 1.

18. A method for control of mites, insects, fungus, mite eggs or insect eggs which comprises applying to a locus to be protected a miticidally, insecticidally, fungicidally or ovicidally effective amount of a compound of claim 2.

19. A method for control of mites, insects, fungus, mite eggs or insect eggs which comprises applying to a locus to be protected a miticidally, insecticidally, fungicidally or ovicidally effective amount of a compound of claim 3.

20. A method for control of mites, insects, fungus, mite eggs or insect eggs which comprises applying to a locus to be protected a miticidally, insecticidally, fungicidally or ovicidally effective amount of a compound of claim 4.

21. A method for control of mites, insects, fungus, mite eggs or insect eggs which comprises applying to a locus to be protected a miticidally, insecticidally, fungicidally or ovicidally effective amount of a compound of claim 5.

22. A method for control of mites, insects, fungus, mite eggs or insect eggs which comprises applying to a locus to be protected a miticidally, insecticidally, fungicidally or ovicidally effective amount of a compound of claim 6.

23. A method for control of mites, insects, fungus, mite eggs or insect eggs which comprises applying to a locus to be protected a miticidally, insecticidally, fungicidally or ovicidally effective amount of a compound of claim 7.

24. A method for control of mites, insects, fungus, mite eggs or insect eggs which comprises applying to a locus to be protected a miticidally, insecticidally, fungicidally or ovicidally effective amount of a compound of claim 8.

25. A method for control of mites, insects, fungus, mite eggs or insect eggs which comprises applying to a locus to be protected a miticidally, insecticidally, fungicidally or ovicidally effective amount of a compound of claim 9.

26. A method for control of mites, insects, fungus, mite eggs or insect eggs which comprises applying to a locus to be protected a miticidally, insecticidally, fungicidally or ovicidally effective amount of a compound of claim 10.

27. A method for control of mites, insects, fungus, mite eggs or insect eggs which comprises applying to a locus to be protected a miticidally, insecticidally, fungicidally or ovicidally effective amount of a compound of claim 11.

28. A method for control of mites, insects, fungus, mite eggs or insect eggs which comprises applying to a locus to be protected a miticidally, insecticidally, fungicidally or ovicidally effective amount of a compound of claim 12.

29. A method for control of mites, insects, fungus, mite eggs or insect eggs which comprises applying to a locus to be protected a miticidally, insecticidally, fungicidally or ovicidally effective amount of a compound of claim 13.

30. A method for control of mites, insects, fungus, mite eggs or insect eggs which comprises applying to a locus to be protected a miticidally, insecticidally, fungicidally or ovicidally effective amount of a compound of claim 14.

31. A method for control of mites, insects, fungus, mite eggs or insect eggs which comprises applying to a locus to be protected a miticidally, insecticidally, fungicidally or ovicidally effective amount of a compound of claim 15.

32. A method for control of mites, insects, fungus, mite eggs or insect eggs which comprises applying to a locus to be protected a miticidally, insecticidally, fungicidally or ovicidally effective amount of the compound of claim 16.

33. An agricultural composition for control of mites, insects, fungus, mite eggs or insect eggs comprising a surfactant, diluent or mixture thereof and a miticidally, insecticidally, fungicidally or ovicidally effective amount of a compound of claim 1.

34. An agricultural composition for control of mites, insects, fungus, mite eggs or insect eggs comprising a surfactant, diluent or mixture thereof and a miticidally, insecticidally, fungicidally or ovicidally effective amount of a compound of claim 2.

35. An agricultural composition for control of mites, insects, fungus, mite eggs or insect eggs comprising a surfactant, diluent or mixture thereof and a miticidally, insecticidally, fungicidally or ovicidally effective amount of a compound of claim 3.

36. An agricultural composition for control of mites, insects, fungus, mite eggs or insect eggs comprising a surfactant, diluent or mixture thereof and a miticidally, insecticidally, fungicidally or ovicidally effective amount of a compound of claim 4.

37. An agricultural composition for control of mites, insects, fungus, mite eggs or insect eggs comprising a surfactant, diluent or mixture thereof and a miticidally, insecticidally, fungicidally or ovicidally effective amount of a compound of claim 5.

38. An agricultural composition for control of mites, insects, fungus, mite eggs or insect eggs comprising a surfactant, diluent or mixture thereof and a miticidally, insecticidally, fungicidally or ovicidally effective amount of a compound of claim 6.

39. An agricultural composition for control of mites, insects, fungus, mite eggs or insect eggs comprising a surfactant, diluent or mixture thereof and a miticidally, insecticidally, fungicidally or ovicidally effective amount of a compound of claim 7.

40. An agricultural composition for control of mites, insects, fungus, mite eggs or insect eggs comprising a surfactant, diluent or mixture thereof and a miticidally, insecticidally, fungicidally or ovicidally effective amount of a compound of claim 8.

41. An agricultural composition for control of mites, insects, fungus, mite eggs or insect eggs comprising a surfactant, diluent or mixture thereof and a miticidally, insecticidally, fungicidally or ovicidally effective amount of a compound of claim 9.

42. An agricultural composition for control of mites, insects, fungus, mite eggs or insect eggs comprising a surfactant, diluent or mixture thereof and a miticidally, insecticidally, fungicidally or ovicidally effective amount of a compound of claim 10.

43. An agricultural composition for control of mites, insects, fungus, mite eggs or insect eggs comprising a surfactant, diluent or mixture thereof and a miticidally, insecticidally, fungicidally or ovicidally effective amount of a compound of claim 11.

44. An agricultural composition for control of mites, insects, fungus, mite eggs or insect eggs comprising a surfactant, diluent or mixture thereof and a miticidally, insecticidally, fungicidally or ovicidally effective amount of a compound of claim 12.

45. An agricultural composition for control of mites, insects, fungus, mite eggs or insect eggs comprising a surfactant, diluent or mixture thereof and a miticidally, insecticidally, fungicidally or ovicidally effective amount of a compound of claim 13.

46. An agricultural composition for control of mites, insects, fungus, mite eggs or insect eggs comprising a surfactant, diluent or mixture thereof and a miticidally, insecticidally, fungicidally or ovicidally effective amount of a compound of claim 14.

47. An agricultural composition for control of mites, insects, fungus, mite eggs or insect eggs comprising a surfactant, diluent or mixture thereof and a miticidally, insecticidally, fungicidally or ovicidally effective amount of a compound of claim 15.

48. An agricultural composition for control of mites, insects, fungus, mite eggs or insect eggs comprising a surfactant, diluent or mixture thereof and a miticidally, insecticidally, fungicidally or ovicidally effective amount of the compound of claim 16.

* * * * *